United States Patent
Katsumura et al.

(10) Patent No.: US 7,084,285 B2
(45) Date of Patent: Aug. 1, 2006

(54) PHOTOAFFINITY-LABELED SPHINGOMYELIN ANALOGS AND PROCESSES THEREOF

(75) Inventors: Shigeo Katsumura, Hyogo-ken (JP); Toshikazu Hakogi, Hyogo-ken (JP); Toshihiko Shigenari, Osaka-fu (JP)

(73) Assignee: Daiso Co., Ltd., Osaka-Fu (JP)

( * ) Notice: Subject to any disclaimer, the term of this patent is extended or adjusted under 35 U.S.C. 154(b) by 0 days.

(21) Appl. No.: 10/934,571

(22) Filed: Sep. 7, 2004

(65) Prior Publication Data
US 2005/0182265 A1    Aug. 18, 2005

(30) Foreign Application Priority Data
Feb. 18, 2004   (JP)   ............... 2004-041750

(51) Int. Cl.
*C07C 231/00*   (2006.01)
(52) U.S. Cl. .............. 554/69; 554/40; 554/68
(58) Field of Classification Search ............ 554/40, 554/68, 69
See application file for complete search history.

(56) References Cited
OTHER PUBLICATIONS

33rd Symposium of Heterocyclic Chemistry (Oct. 15-17, 2003), Abstract (published on Sep. 19, 2003).

*Primary Examiner*—Deborah D. Carr
(74) *Attorney, Agent, or Firm*—Wenderoth, Lind & Ponack, L.L.P.

(57) ABSTRACT

A photoaffinity-labeled sphingomyelin analog of the following formula:

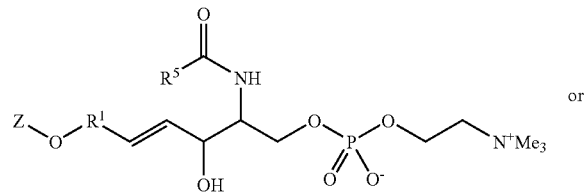

(1)

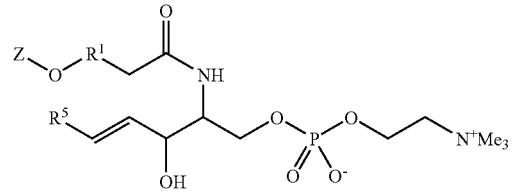

(2)

wherein $R^1$ is $C_{1-20}$ alkylene group, $R^5$ is $C_{1-20}$ alkyl group, aryl group or $C_{1-6}$ alkyl group substituted by aryl group, Z is photoaffinity-labeled group and Me is methyl group, or an optically active compound thereof.

7 Claims, No Drawings

PHOTOAFFINITY-LABELED SPHINGOMYELIN ANALOGS AND PROCESSES THEREOF

TECHNICAL FIELD

The present invention relates to photoaffinity-labeled sphingomyelin analogs and processes thereof.

BACKGROUND OF THE INVENTION

Metabolites of sphingomyelin, sphingolipids such as ceramide, sphingosine or sphingosine 1-phosphate, participate in intracellular signal translation, such as apoptosis, cell proliferation, PKC inhibition, etc., and therefore the metabolites have drawn the great attention. From the fact, the enzyme, sphingomyelinase which converts sphingomyelin to ceramide is considered to be a very important enzyme.

However, the mechanism of action and higher-order structure of this enzyme is not elucidated and therefore, such a substance as useful for a resolution of the mechanism has been desired.

DISCLOSURE OF INVENTION

The present inventors designed following compounds and prepared them in order to invest the mechanism of action of sphingomyelinase.

Namely the present inventors have intensively studied and as a result, have succeeded in synthesis of photoaffinity-labeled sphingomyelin analogs suitable to the present object.

A photoaffinity-labeled sphingomyelin analog of the present invention is represented by the following formula,

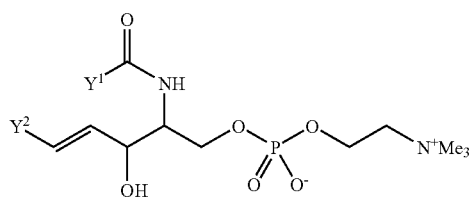
(1-2)

wherein $Y^1$ and $Y^2$ are different from each other and are $R^5$ or $Z$—$O$—$R^1$, and $R^5$, $Z$, $R^1$ and Me are the same as mentioned below, or an optically active compound thereof.

More concretely the present invention relates to a photoaffinity-labeled sphingomyelin analog represented by the following formula,

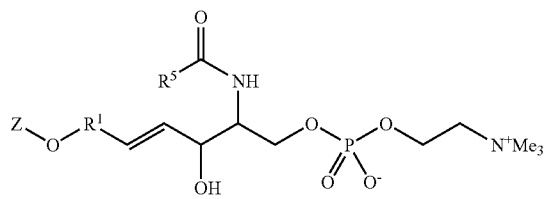
(1)

wherein $R^1$ is $C_{1-20}$ alkylene group, preferably $C_{7-16}$ alkylene group, $R^5$ is $C_{1-20}$ alkyl group, preferably $C_{7-16}$ alkyl group, aryl group or $C_{1-16}$ alkyl group substituted by aryl group, Z is not photoaffinity-labeled group and Me is methyl group, or an optically active compound thereof.

The present invention also relates to a photoaffinity-labeled sphingomyelin analog represented by the following formula,

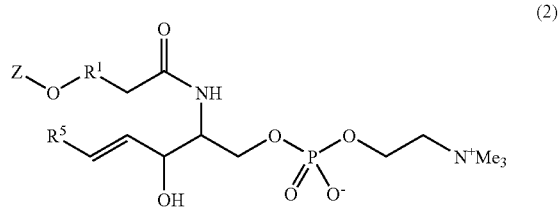
(2)

wherein $R^1$ is $C_{1-20}$ alkylene group, preferably $C_{7-16}$ alkylene group, $R^5$ is $C_{1-20}$ alkyl group, preferably $C_{7-16}$ alkyl group, aryl group or $C_{1-16}$ alkyl group substituted by aryl group, Z is not photoaffinity-labeled group and Me is methyl group, or an optically active compound thereof.

The present invention also relates to a process for preparing a photoaffinity-labeled sphingomyelin analog of the following formula,

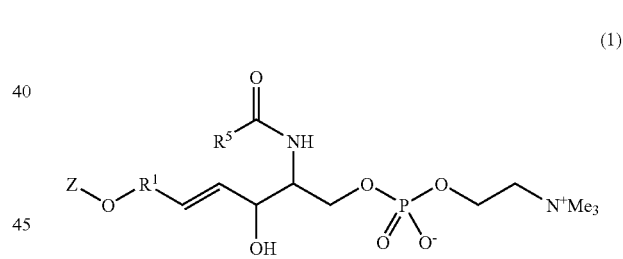
(1)

wherein $R^1$ is $C_{1-20}$ alkylene group, $R^5$ is $C_{1-20}$ alkyl group, aryl group or $C_{1-6}$ alkyl group substituted by aryl group, Z is photoaffinity-labeled group and Me is methyl group, or an optically active compound thereof, which comprises deprotecting hydroxy group (deletion of $P^1$) of the compound of the following formula (3),

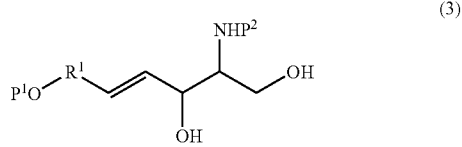
(3)

wherein $P^1$ is hydroxy protecting group, $P^2$ is amino protecting group, and $R^1$ is the same as defined above, to prepare a triol compound represented by the following formula (4),

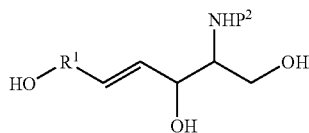

wherein $R^1$ and $P^2$ are the same defined above, acetalizing two hydroxy groups of the compound (4) to prepare a compound of the following formula (5),

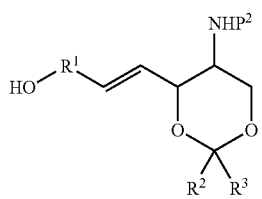

wherein $R^2$ and $R^3$ are the same or different and are hydrogen atom, $C_{1-4}$ alkyl group or phenyl group, or $R^2$ and $R^3$ may be taken together to form $C_{3-6}$ cycloalkyl group, and $R^1$ and $P^2$ are the same as defined above, reacting the compound (5) with a compound having photo-affinity-labeled group, subjecting the compound to deacetonide reaction to prepare a compound of the following formula (6),

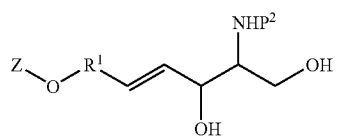

wherein $R^1$, $P^2$ and Z are the same as defined above, and then reacting the compound (6) with 2-halogenoethyl dialkyl phosphite to prepare a compound of the following formula (7),

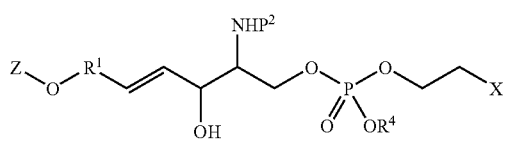

wherein $R^4$ is $C_{1-6}$ alkyl group, X is halogen, and $R^1$, $P^2$ and Z are the same as defined above, deprotecting amino group (deletion of $P^2$) of the compound (7) and then subjecting the compound to amidation reaction to prepare a compound of the following formula (8),

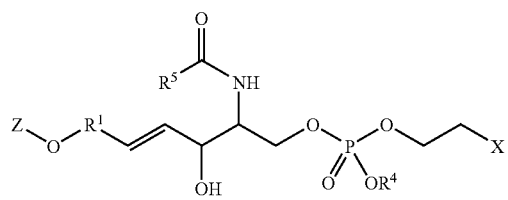

wherein $R^5$, X, Z, $R^1$ and $R^4$ are the same as defined above, substituting X of the compound (8) with trimethylamine, and hydrolyzing the phosphate to prepare the compound (1).

The process for the preparation of the compound (1) can be shown by the following reaction scheme.

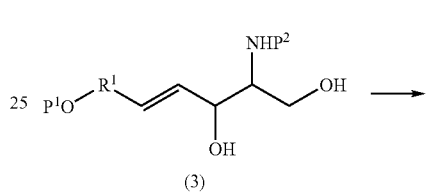

-continued

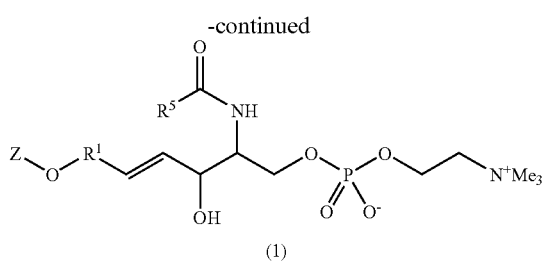

(1)

wherein $R^1$–$R^5$, $P^1$, $P^2$, X, Z and Me are the same as defined above.

Each of steps of the process for preparing the compound (1) is explained in detail as follows.

The compound (3) is prepared, for example by the method disclosed in Japanese patent Publication A 2003-261794.

Hydroxy of the compound (3) is deprotected to give the compound (4). The deprotecting reaction is carried out depending on the kind of the protecting group in accordance with the conventional method. For example, when the protecting group is tetrahydropyranyl group, the deprotecting reaction is carried out in a solvent such as methanol, etc., in the presence of catalyst, such as p-toluenesulfonic acid, etc.

Two hydroxy groups of the compound (4) are acetalized in the presence of acid catalyst to give the compound (5). The acid includes an organic acid such as p-toluenesulfonic acid, pyridinium paratoluenesulfonate, camphorsulfonic acid, etc., a mineral acid, such as hydrochloric acid, sulfuric acid, phosphoric acid, etc., and a Lewis acid, such as boron trifluoride-diethyl ether complex, etc.

The amount of the acid is preferably 0.01~1 mole to the substrate, more preferably 0.01~0.1 mole.

In this reaction, the following acetalization agents are used.

Formaldehyde is used in case of the compound (5) wherein $R^2$ and $R^3$ are hydrogen atom. Benzophenone is used in case of the compound (5) wherein $R^2$ and $R^3$ are phenyl group. Cyclohexanone is used in case of the compound (5) wherein $R^2$ and $R^3$ are taken together to form a 6 membered ring. Further acetone, 2,2-dimethoxypropane and 2-methoxypropene are preferably used in case of the compound (5) wherein $R^2$ and $R^3$ are methyl group.

The solvent to be used includes preferably a hydrocarbon-solvent, such as hexane, benzene, toluene, etc., an aprotic polar solvent, such as N,N-dimethylformamide, dimethyl sulfoxide, etc., an ester-solvent, such as ethyl acetate, butyl acetate, etc., an ether-solvent, such as tetrahydrofuran, 1,4-dioxane, 1,2-dimethoxyethane, diglyme, triglyme, diethylene glycol monomethyl ether, etc., a nitrile-solvent, such as acetonitrile, etc., and a halogen-solvent, such as dichloromethane, 1,2-dichloroethane, etc., and the acetalization agent may be served as a solvent.

The reaction is carried out preferably at 0° C. to the refluxing temperature of the solvent, more preferably at 0° C. to 25° C.

The compound (5) and a compound photoaffinity-labeled group are reacted and the reacted compound is subjected to deacetonide reaction to give the compound (6).

The compound having photoaffinity-labeled group is not limited as long as photoaffinity-labeled group is present within the molecule. For example when using 4-(3-trifluoromethyl-3H-diazirin-3-yl)-phenol, the said compound is prepared in the same manner as described in Chem. Pharm. Bull., 826 (1994).

The reagent used in this reaction includes a combination of an azodicarboxylate (e.g., diethyl azodicarboxylate, diisopropyl azodicarboxylate, etc.) and a phosphine compound (e.g., triphenylphosphine, tributylphosphine, etc.).

The solvent to be used includes a hydrocarbon-solvent, such as hexane, benzene, toluene, etc., an aprotic polar solvent, such as N,N-dimethylformamide, dimethyl sulfoxide, etc., an ester-solvent, such as ethyl acetate, butyl acetate, etc., an ether-solvent, such as tetrahydrofuran, 1,4-dioxane, 1,2-dimethoxyethane, diglyme, triglyme, diethylene glycol monomethyl ether, etc., a ketone-solvent, such as acetone, methyl ethyl ketone, methyl isobutyl ketone, etc., a nitrile-solvent, such as acetonitrile, etc., a halogen-solvent, such as dichloromethane, 1,2-dichloroethane, etc., and a mixture thereof.

The reaction is carried out preferably at −78° C. to the refluxing temperature of the solvent, more preferably at 0° C. to 25° C.

Deacetonidation is carried out in accordance with a known method, for example the deacetonidation is carried out in an alcohol-solvent, such as methanol, ethanol, etc., in the presence of a mineral acid such as diluted hydrochloric acid, diluted sulfuric acid, etc., or an organic acid such as p-toluenesulfonic acid, pyridinium paratoluenesulfonate, etc.

The reaction is carried out preferably at −78° C. to the refluxing temperature of the solvent, more preferably 0° C. to 50° C.

The compound (6) is reacted with 2-halogenoethyl dialkyl phosphite in the presence of carbon tetrabromide to give the compound (7). As 2-halogenoethyl dialkyl phoaphite, 2-chloroethyl dimethyl phosphite, and 2-bromoethyl dimethyl phosphite are preferably illustrated.

The amount of 2-halogenoethyl dialkyl phosphite is preferably 1~3 moles to the substrate, more preferably 1~1.5 moles.

The solvent to be used includes a hydrocarbon-solvent, such as hexane, benzene, toluene, etc., an aprotic polar solvent, such as N,N-dimethylformamide, dimethyl sulfoxide, etc., an ester-solvent, such as ethyl acetate, butyl acetate, etc., an ether-solvent, such as tetrahydrofuran, 1,4-dioxane, 1,2-dimethoxyethane, diglyme, triglyme, diethylene glycol monomethyl ether, etc., a ketone-solvent, such as acetone, methyl ethyl ketone, methyl isobutyl ketone, etc., nitrile-solvent, such as acetonitrile, etc., a halogen-solvent, such as dichloromethane, 1,2-dichloroethane, etc., and a mixture thereof.

The base to be used in this reaction includes preferably a tertiary amine, such as triethylamine, ethyl diisopropylamine, N,N-dimethylaniline, N,N-diethylaniline, pyridine, picoline, lutidine, collidine, 4-N,N-dimethylaminopyridine, etc., more preferably pyridine, which can be served as a solvent.

The reaction is carried out preferably at 0° C. to the refluxing temperature of the solvent, more preferably at 0° C. to 25° C.

Amino group of the compound (7) is deprotected and then, the deprotected compound is amidated to give the compound (8).

The deprotection reaction of amino group is carried out by the conventional method. For example when $P^2$ is t-butoxycarbonyl group, trifluoroacetic acid or diluted hydrochloric acid may be used.

The preferable reagent used for this amidation includes $C_{2-21}$ cyclic or noncyclic acylchloride, such as acetylchloride, propionylchloride, butyrylchloride, valerylchloride, hexanoylchloride, benzoylchloride, etc.

The amount of the acylchloride is preferably 1~3 moles to the substrate, more preferably 1~1.5 moles.

The preferable solvent to be used includes hydrocarbon-solvent hexane, benzene, toluene, etc., an aprotic polar solvent, such as N,N-dimethylformamide, dimethyl sulfoxide, etc., an ester-solvent, such as ethyl acetate, butyl acetate, etc., an ether-solvent, such as tetrahydrofuran, 1,4-dioxane, 1,2-dimethoxyethane, diglyme, triglyme, diethylene glycol monomethyl ether, etc., a ketone-solvent such as acetone, methyl ethyl ketone, methyl isobutyl ketone, etc., a nitrile-solvent, such as acetonitrile, etc., a halogen-solvent, such as dichloromethane, 1,2-dichloroethane, etc., water and a mixture thereof.

The amidation reaction is carried out at 0° C. to the refluxing temperature of the solvent, preferably at 0° C. to 25° C.

X of the compound (8) is substituted by trimethylamine, followed by hydrolysis to give a photoaffinity-labeled sphingomyelin analog (1).

The solvent to be used includes preferably an alcohol-solvent, such as methanol, ethanol, etc., a hydrocarbon-solvent hexane, benzene, toluene, etc., an aprotic polar solvent, such as N,N-dimethylformamide, dimethyl sulfoxide, etc., an ester-solvent, such as ethyl acetate, butyl acetate, etc., an ether-solvent, such as tetrahydrofuran, 1,4-dioxane, 1,2-dimethoxyethane, diglyme, triglyme, diethylene glycol monomethyl ether, etc., a ketone-solvent, such as acetone, methyl ethyl ketone, methyl isobutyl ketone, etc., a nitrile-solvent, such as acetonitrile, etc., a halogen-solvent, such as dichloromethane, 1,2-dichloroethane, etc., water and a mixture thereof, more preferably an alcohol-solvent, such as methanol, ethanol, etc.

The reaction is carried out preferably at 0° C. to the refluxing temperature of the solvent, more preferably at 0° C. to 25° C.

The present invention also relates to a process for preparing a photoaffinity-labeled sphingomyelin analog of the following formula (2),

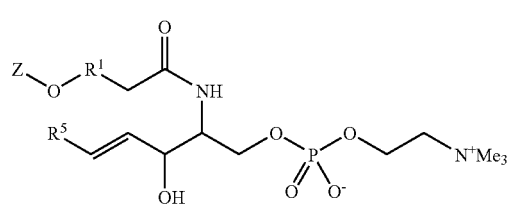

(2)

wherein $R^1$ is $C_{1-20}$ alkylene group, $R^5$ is $C_{1-20}$ alkyl group, aryl group or $C_{1-6}$ alkyl group substituted by aryl group, Z is photoaffinity-labeled group and Me is methyl group, or an optically active compound thereof, which comprises reacting a compound of the formula (9),

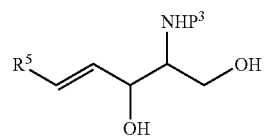

(9)

wherein $R^5$ is the same as defined above and $P^3$ is amino protecting group, with 2-halogenoethyl dialkyl phosphite to prepare a compound of the following formula (10),

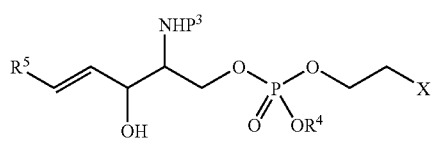

(10)

wherein $R^5$ and $P^3$ are the same as defined above and $R^4$ is $C_{1-6}$ alkyl group and X is a halogen atom, deprotecting amino group (deletion of $P^3$) of the compound (10), reacting the deprotected compound with a compound of the following formula (11),

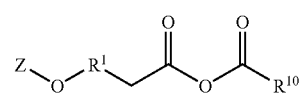

(11)

wherein $R^1$ and Z are the same as defined above and $R^{10}$ is $C_{1-6}$ alkyl group, to prepare a compound of the formula (12),

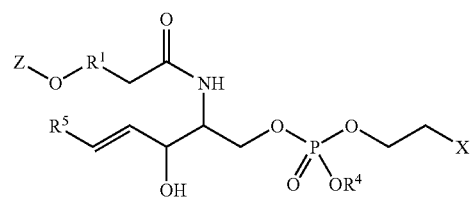

(12)

wherein X, Z, $R^4$, $R^5$ and $R^1$ are the same as defined above, substituting X of the compound (12) with trimethylamine, and then hydrolyzing the phosphate to prepare the compound (2).

The process for the preparation of the compound (2) can be shown by the following reaction scheme.

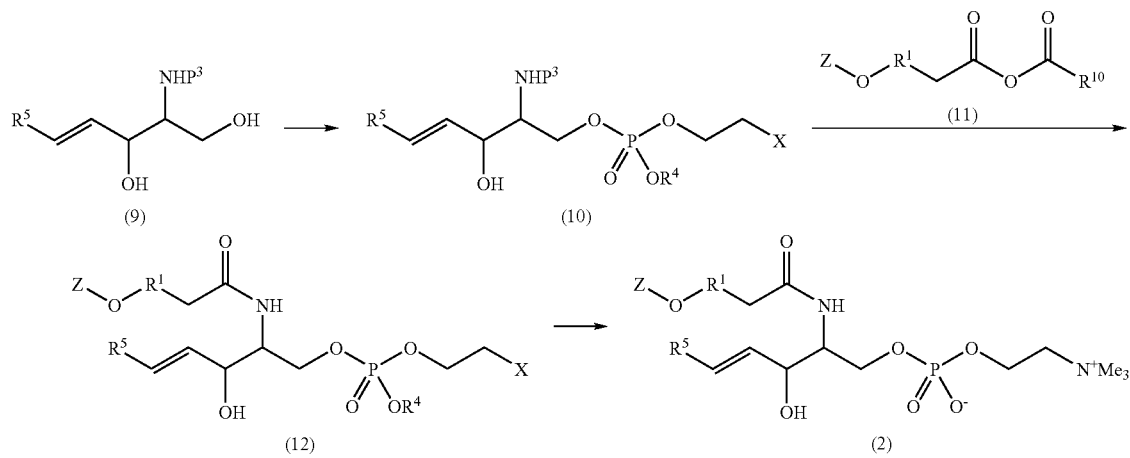

wherein $P^3$, $R^{10}$, $R^4$, $R^6$, $R^7$, X, Z and Me are the same as defined above.

Each of steps of the process for preparing the compound (2) is explained in detail as follows.

The compound (9), for example wherein $R^6$ is $C_{13}H_{27}$, is prepared by protecting amino group of sphingosine commercially available.

The compound (9) is reacted with 2-halogenoethyl dialkyl phosphite in the presence of carbon tetrabromide to give the compound (10). As 2-halogenoethyl dialkyl phosphite, 2-chloroethyl dimethyl phosphite and 2-bromoethyl dimethyl phosphite are preferably illustrated.

The amount of 2-halogenoethyl dialkyl phosphite is preferably 1~3 moles to the substrate, more preferably 1~1.5 moles.

The solvent to be used includes preferably a hydrocarbon-solvent, such as hexane, benzene, toluene, etc., an aprotic polar solvent, such as N,N-dimethylformamide, dimethyl sulfoxide, etc., ester-solvent, such as ethyl acetate, butylacetate, etc., ether-solvent, such as tetrahydrofuran, 1,4-dioxane, 1,2-dimethoxyethane, diglyme, triglyme, diethylene glycol monomethyl ether, etc., a ketone-solvent, such as acetone, methyl ethyl ketone, methyl isobutyl ketone, etc., a nitrile-solvent, such as acetonitrile, etc., a halogen-solvent, such as dichloromethane, 1,2-dichloroethane, etc., and a mixture thereof.

The base to be used in this reaction includes preferably a tertiary amine, such as triethylamine, ethyl diisopropylamine, N,N-dimethylaniline, N,N-diethylaniline, pyridine, picoline, lutidine, collidine, 4-N,N-dimethylaminopyridine, etc., more preferably pyridine, which may be served as a solvent.

The reaction is carried out preferably at 0° C. to the refluxing temperature of the solvent, more preferably at 0° C. to 25° C.

Amino of the compound (10) is deprotected and then, the deprotected compound is amidated with the compound (11) to give the compound (12).

The deprotection reaction is carried out by the conventional method. For example when $P^2$ is t-butoxycarbonyl group, trifluoroacetic acid or diluted hydrochloric acid can be preferably used.

The base used for the amidation reaction includes preferably an alkali metal or alkaline earth metal carbonate, such as lithium carbonate, sodium carbonate, potassium carbonate, calcium carbonate, cesium carbonate, etc., an alkali metal or alkaline earth metal hydrogencarbonate, such as lithium hydrogencarbonate, sodium hydrogencarbonate, potassium hydrogencarbonate, etc., a tertiary amine, such as triethylamine, ethyl diisopropylamine, N,N-dimethylaniline, N,N-diethylaniline, pyridine, picoline, lutidine, colline, 4-N, N-dimethylaminopyridine, etc., more preferably a carbonate, such as lithium carbonate, sodium carbonate, potassium carbonate, calcium carbonate, cesium carbonate, etc.

The preferable solvent to be used in this reaction includes a hydrocarbon-solvent, such as hexane, benzene, toluene, etc., an aprotic polar solvent, such as N,N-dimethylformamide, dimethyl sulfoxide, etc., an ester-solvent, such as ethyl acetate, butyl acetate, etc., an ether-solvent, such as tetrahydrofuran, 1,4-dioxane, 1,2-dimethoxyethane, diglyme, triglyme, diethylene glycol monomethyl ether, etc., a ketone-solvent, such as acetone, methyl ethyl ketone, methyl isobutyl ketone, etc., a nitrile-solvent, such as acetonitrile, etc., a halogen-solvent, such as dichloromethane, 1,2-dichloroethane, etc., water and a mixture thereof.

The reaction is carried out preferably at 0° C. to the refluxing temperature of the solvent, more preferably at 0° C. to 25° C.

X of the compound (12) is substituted by trimethylamine, followed by hydrolysis to give a sphingomyelin analog having photoaffinity-labeled group on the acyl group (2).

The solvent includes preferably an alcohol-solvent, such as methanol, ethanol, etc., hydrocarbon-solvent, such as hexane, benzene, toluene, etc., an aprotic polar solvent, such as N,N-dimethylformamide, dimethyl sulfoxide, etc., an ester-solvent, such as ethyl acetate, butyl acetate, etc., an ether-solvent, such as tetrahydrofuran, 1,4-dioxane, 1,2-dimethoxyethane, diglyme, triglyme, diethylene glycol monomethyl ether, etc., a ketone-solvent, such as acetone, methyl ethyl ketone, methyl isobutyl ketone, etc., a nitrile-solvent, such as acetonitrile, etc., a halogen-solvent, such as dichloromethane, 1,2-dichloroethane, etc., water and a mixture thereof, more preferably an alcohol-solvent, such as methanol, ethanol, etc.

The reaction is carried out preferably at 0° C. to the refluxing temperature of the solvent, more preferably at 0° C. to 25° C.

The starting compound of the above process for preparing the compound (2), namely a compound of the following formula (11),

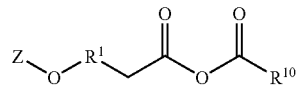 (11)

wherein Z, R$^1$ and R$^{10}$ are the same as defined above, is prepared by subjecting a compound of the following formula (13),

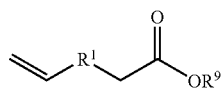 (13)

wherein R$^9$ is C$_{1-6}$ alkyl group and R$^1$ is the same as defined above, to ozonolysis to prepare an aldehyde compound, reducing the compound to prepare a compound of the following formula (14),

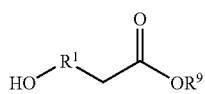 (14)

wherein R$^1$ and R$^9$ are the same as defined above, reacting the compound (14) with a compound having photoaffinity-labeled group to prepare a compound of the following formula (15),

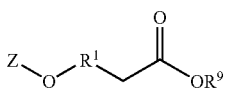 (15)

wherein Z, R$^1$ and R$^9$ are the same as defined above, hydrolyzing the compound (15) and converting the product to an acid anhydride to prepare the compound (11).

The process for the preparation of the compound (11) can be shown by the following reaction scheme.

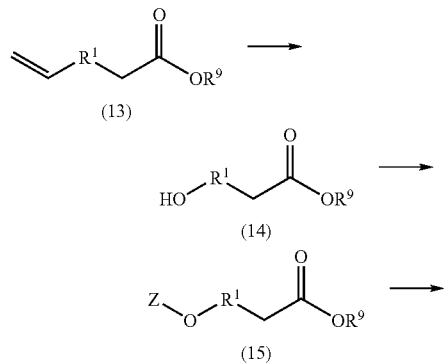

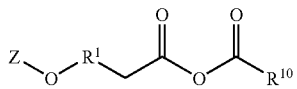

wherein R$^9$ is C$_{1-6}$ alkyl group, and R$^1$, R$^{10}$ and Z are the same defined above.

The compound (13) is subjected to ozonolysis according to the conventional method and then to reduction to prepare the compound (14).

The preferable solvent used for ozonolysis includes a hydrocarbon-solvent, hexane, benzene, toluene, etc., an ether-solvent tetrahydrofuran, 1,4-dioxane, 1,2-dimethoxyethane, diglyme, triglyme, diethylene glycol monomethyl ether, etc., a nitrile-solvent, such as acetonitrile, etc., a halogen-solvent, such as dichloromethane, 1,2-dichloroethane, etc., an alcohol-solvent, such as methanol, ethanol, etc., and a mixture thereof.

The ozonolysis is carried out preferably at −78° C. to 25° C., more preferably at 78° C. to 0° C.

The reduction reagent used for reducing aldehyde group is not limited as long as the reagent can reduce aldehyde group to give an alcohol, such as lithium aluminium hydride, etc.

The preferable solvent used for reduction includes a hydrocarbon-solvent, such as hexane, benzene, toluene, etc., an ether-solvent, such as tetrahydrofuran, 1,4-dioxane, 1,2-dimethoxyethane, diglyme, triglyme, diethylene glycol monomethyl ether, etc., a nitrile-solvent such as acetonitrile, etc., a halogen-solvent, such as dichloromethane, 1,2-dichloroethane, etc., an alcohol-solvent, such as methanol, ethanol, etc., and a mixture thereof.

The reduction is carried out at −78° C. to the refluxing temperature of the solvent, preferably −78° C. to 25° C.

The compound (15) is prepared by reacting the compound (14) and a compound having photoaffinity-labeled group. The compound having photoaffinity-labeled group is not limited as long as photoaffinity-labeled group is present within the molecule. For example, when using 4-(3-trifluoromethyl-3H-diazirin-3-yl)-phenol, the said compound is prepared in the same manner as described in Chem. Pharm. Bull., 826 (1994).

The reagent used in this reaction includes a combination of an azodicarboxylate (e.g., diethyl azodicarboxylate, diisopropyl azodicarboxylate, etc.) and a phosphine compound (e.g., triphenylphosphine, tributylphosphine, etc.).

The preferable solvent includes a hydrocarbon-solvent, such as hexane, benzene, toluene, etc., an aprotic polar solvent, such as N,N-dimethylformamide, dimethyl sulfoxide, etc., ester-solvent, such as ethyl acetate, butyl acetate, etc., an ether-solvent, such as tetrahydrofuran, 1,4-dioxane, 1,2-dimethoxyethane, diglyme, triglyme, diethylene glycol monomethyl ether, etc., a ketone-solvent, such as acetone, methyl ethyl ketone, methyl isobutyl ketone, etc., nitrile-solvent such as acetonitrile, etc., a halogen-solvent, such as dichloromethane, 1,2-dichloroethane, etc., and a mixture thereof.

The reaction is carried out preferably at −78° C. to the refluxing temperature of the solvent, more preferably at 0° C. to 25° C.

The compound (15) is subjected to hydrolysis and then is converted to the acid anhydride to prepare the compound (11).

The reagent used for hydrolysis includes preferably an alkali metal or alkaline earth metal hydroxide, such as lithium hydroxide, sodium hydroxide, potassium hydroxide, calcium hydroxide, etc., an alkali metal or alkaline earth metal carbonate, such as lithium carbonate, sodium carbonate, potassium carbonate, calcium carbonate, cesium carbonate, etc., an alkali metal or alkaline earth metal hydrogencarbonate such as lithium hydrogencarbonate, sodium hydrogencarbonate, potassium hydrogencarbonate, etc., an alkali metal or alkaline earth metal hydride, such as potassium hydride, sodium hydride, calcium hydride, etc., more preferably an alkali metal or alkaline earth metal hydroxide, such as lithium hydroxide, sodium hydroxide, potassium hydroxide, calcium hydroxide, etc.

The preferable solvent includes a hydrocarbon-solvent, such as hexane, benzene, toluene, etc., an aprotic polar solvent, such as N,N-dimethylformamide, dimethyl sulfoxide, etc., an ether-solvent, such as tetrahydrofuran, 1,4-dioxane, 1,2-dimethoxyethane, diglyme, triglyme, diethylene glycol monomethyl ether, etc., a ketone-solvent, such as acetone, methyl ethyl ketone, methyl isobutyl ketone, etc., a nitrile-solvent such as acetonitrile, etc., a halogen-solvent, such as dichloromethane, 1,2-dichloroethane, etc., an alcohol-solvent, such as methanol, ethanol, etc., and a mixture thereof.

The reagent used when preparing an acid anhydride includes $C_{1-6}$ alkanoic acid chloride, such as acetylchloride, butyrylchloride, pivaloylchloride, etc.

The preferable base to be used in this reaction includes a tertiary amine, such as triethylamine, ethyl diisopropylamine, N,N-dimethylaniline, N,N-diethylaniline, pyridine, picoline, lutidine, collidine, 4-N,N-dimethylaminopyridine, etc.

The preferable solvent to be used in this reaction includes a hydrocarbon-solvent, such as hexane, benzene, toluene, etc., an aprotic polar solvent, such as N,N-dimethylformamide, dimethyl sulfoxide, etc., an ether-solvent, such as tetrahydrofuran, 1,4-dioxane, 1,2-dimethoxyethane, diglyme, triglyme, diethylene glycol monomethylether etc., a ketone-solvent such as acetone, methyl ethyl ketone, methyl isobutyl ketone, etc., a nitrile-solvent, such as acetonitrile, etc., a halogen-solvent, such as dichloromethane, 1,2-dichloroethane, etc., and a mixture thereof.

An optically active photoaffinity-labeled sphingomyelin analog (1) is prepared in highly optical purity by using an optically active compound (3) as a starting material.

A sphingomyelin analog (2) having photoaffinity-labeled group on optically active acyl group can be also prepared in highly optical purity by using an optically active compound (9) as a starting material.

The present invention is illustrated by the following examples, but is not limited by these examples.

EXAMPLE 1

Synthesis of Triol (17)

To Diol (16) (1.60 g, 3.60 mmol) in methanol (18.0 mL) was added at room temperature p-toluenesulfonic acid monohydrate (687 mg, 3.60 mL), and the mixture was stirred at the same temperature for 30 minutes. To the reaction mixture was added an aqueous saturated sodium hydrogencarbonate solution and the mixture was neutralized. The solution was concentrated under reduced pressure and the residue was extracted with ethyl acetate. The organic layer was washed with an aqueous saturated sodium chloride solution, dried over anhydrous magnesium sulfate and concentrated under reduced pressure. The residue was subjected to silica gel chromatography (from 66% to 75% ethyl acetate in hexane) to give Triol (17) (1.20 g, 92.4%).

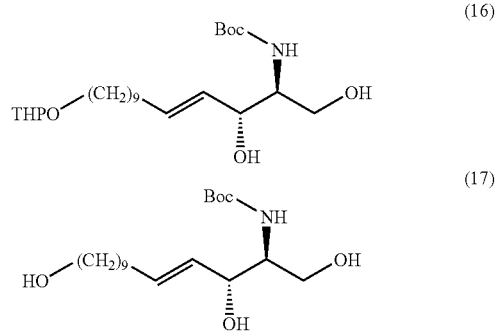

$[\alpha]_D^{22.0}$ −0.645 (c=1.102, $CHCl_3$) IR (KBr disk): 3339.08, 1682.08, 1527.76, 1172.83, 667.43 $cm^{-1}$ $^1H$ NMR ($CDCl_3$, 400 MHz) δ: 5.76 (dtd, J=1.2, 6.8, 15.4 Hz, 1H), 5.53 (ddd, J=1.2, 6.4, 15.4 Hz, 1H), 5.35 (d, J=6.3 Hz, 1H), 4.28 (m, 1H), 3.91 (m, 1H ), 3.68 (m, 2H), 3.63 (t, J=6.6 Hz, 2H), 3.15 (brs, 1H), 3.11 (brs, 1H), 2.05 (q, J=6.8 Hz, 2H), 1.97 (m, 2H), 1.55 (q, J=6.6 Hz, 2H), 1.45 (s, 9H), 1.37–1.28 (m, 12H); $^{13}C$ NMR ($CDCl_3$, 100 MHz) δ: 156.3, 133.9, 129.0, 79.8, 74.6, 62.9, 62.5, 32.6, 32.2, 29.4, 29.2, 29.2, 28.9, 28.4, 25.6.

EXAMPLE 2

Synthesis of Acetonide (18)

To Triol (17) (3.59 g, 9.98 mmol) in DMF (49.9 mL) were added at 0° C., 2,2-dimethoxypropane (3.68 mL, 29.9 mmol) and camphorsulfonic acid (1.16 g, 4.99 mmol), and the mixture was stirred for 4 hours at room temperature. The reaction mixture was cooled to 0° C., followed by adding water and was stirred for 5 minutes. The reaction mixture was neutralized with an aqueous saturated sodium hydrogencarbonate solution, and extracted with ethyl acetate. The organic layer was washed with an aqueous saturated sodium hydrogencarbonate solution, dried over anhydrous magnesium sulfate and concentrated under reduced pressure. The residue was purified with silica gel column chromatography (from 33% to 50% ethyl acetate in hexane) to give Acetonide (18) (3.83 g, 96.1%).

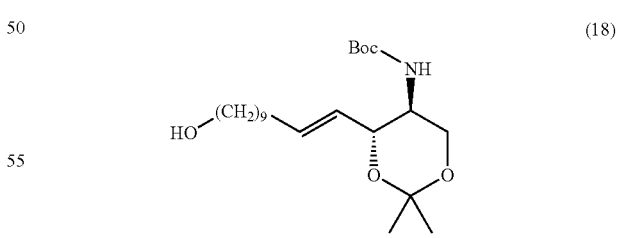

$[\alpha]_D^{22.0}$ 1.26 (c=0.764, $CHCl_3$) IR (KBr disk): 3402.74, 1687.87, 1514.26, 1170.90, 1014.65 $cm^{-1}$ $^1H$ NMR ($CDCl_3$, 400 MHz) δ: 5.77 (td, J=6.6, 15.4 Hz, 1H), 5.43 (dd, J=7.6, 15.4 Hz, 1H), 4.37 (m, 1H), 3.97 (m, 2H ), 3.63 (t, J=6.6 Hz, 2H), 3.62 (m, 1H), 3.49 (m, 1H), 2.04 (m, 2H), 1.79–1.28 (m, 29H); $^{13}C$ NMR ($CDCl_3$, 100 MHz) δ: 155.1, 136.3, 134.1, 127.2, 126.3, 98.6, 77.2, 74.6, 63.0, 62.9, 48.9, 32.7, 32.3, 29.4, 29.3, 29.3, 29.1, 28.8, 28.7, 28.3, 28.3, 25.7.

EXAMPLE 3

Synthesis of N-Boc-4-(3-trifluoromethyl-3H-diazirin-3-yl)-phenoxy (TFDP)-sphingosine (20)

To Acetonide (18) (2.50 g, 6.26 mmol) in THF (25.0 mL) were added at 0° C. triphenylphosphine (2.46 g, 9.39 mmol) and diisopropyl azodicarboxylate (1.85 mL, 9.39 mmol), followed by adding Phenol (19) (1.90 g, 9.39 mmol) in THF (6.3 mL) at room temperature. After the mixture was stirred for 1 hour, the solvent of the reaction mixture was removed under reduced pressure. The residue was purified with silica gel column chromatography (25% ethyl acetate in hexane) to give crude TFDP-acetonide. To thus obtained crude TFDP-acetonide in methanol (62.6 mL) was added at 0° C. p-toluenesulfonic acid monohydrate (1.19 g, 6.26 mmol) and the mixture was stirred at the same temperature for 1 hour. To the reaction mixture was added an aqueous saturated sodium hydrogencarbonate solution to neutralize it. The solution was concentrated under reduced pressure and the residue was extracted with ethyl acetate. The organic layer was washed with an aqueous saturated sodium chloride solution, dried over anhydrous magnesium sulfate and concentrated under reduced pressure. The residue was purified with silica gel column chromatography (from 33% to 50% ethyl acetate in hexane) to give N-Boc-TFDP-sphingosine (20) (2.47 g, 72.5%).

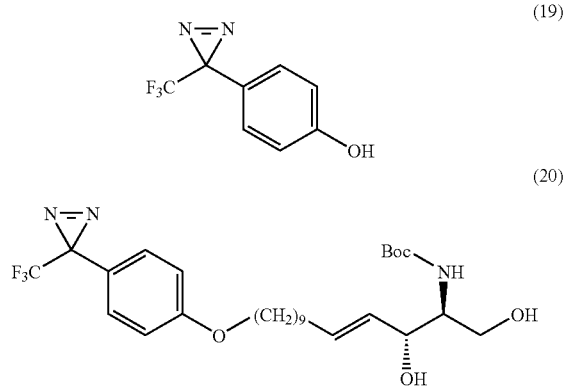

$[\alpha]_D^{22.0}$ −2.17 (c=1.021, CHCl$_3$) IR (KBr disk): 3366.09, 1662.79, 1520.04, 1182.47, 823.68 cm$^{-1}$ $^1$H NMR (CDCl$_3$, 400 MHz) δ: 7.13 (md, J=9 Hz, 2H), 6.89 (md, J=9 Hz, 2H), 5.77 (dtd, J=1.0, 6.8, 15.4 Hz, 1H), 5.53 (dd, J=6.4, 15.4 Hz, 1H), 5.32 (brs, 1H), 4.31 (m, 1H), 3.94 (t, J=6.6 Hz, 2H), 3.93 (m, 1H), 3.71 (m, 1H), 3.60 (m, 1H), 2.76 (brm, 2H), 2.05 (q, J=6.8, 2H), 1.77 (m, 2H), 1.49–1.28 (m, 21H); $^{13}$C NMR (CDCl$_3$, 100 MHz) δ: 160.2, 156.2, 134.0, 129.0, 128.1, 122.2 (q, J$_{C-F}$=274.6 Hz), 120.6, 114.8, 79.8, 74.8, 68.1, 64.4, 62.6, 55.4, 34.2, 32.2, 29.4, 29.3, 29.3, 29.1, 29.1, 28.4, 25.9.

EXAMPLE 4

Synthesis of N-Boc-phosphate (21)

To carbon tetrabromide (1.37 g, 4.14 mmol) in pyridine (13.8 mL) was added 2-bromoethyl dimethyl phosphite (0.62 mL, 4.14 mmol) at 0° C., followed by adding N-Boc-TFDP-sphingosine (20) (1.50 g, 2.76 mmol). The mixture was stirred for 3.5 hours while gradually rising to room temperature. The reaction mixture was filtered and neutralized with 2N-hydrochloric acid. Then the mixture was extracted with ethyl acetate and the organic layer was washed with 2N-hydrochloric acid, an aqueous saturated sodium hydrogencarbonate solution and an aqueous saturated aqueous sodium chloride solution, successively. The mixture was dried over anhydrous magnesium sulfate, concentrated under reduced pressure and the residue was purified with silica gel column chromatography (from 33% to 50% ethyl acetate in hexane) to give N-Boc-phosphate (21) (1.49 g, 72.4%).

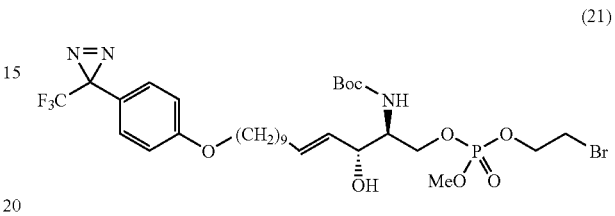

$[\alpha]_D^{22.0}$ 2.44 (c=1.078, CHCl$_3$) IR (NaCl neat): 3406.60, 1712.94, 1518.11, 1257.70, 1055.16 cm$^{-1}$ $^1$H NMR (CDCl$_3$, 400 MHz) δ: 7.13 (md, J=9 Hz, 2H), 6.89 (md, J=9 Hz, 2H), 5.76 (dtd, J=0.7, 6.7, 15.4 Hz, 1H), 5.50 (dd, J=7.1, 15.4 Hz, 1H), 5.06 (brs, 1H), 4.36–4.31 (m, 3H), 4.16 (m, 2H), 3.94 (t, J=6.6 Hz, 2H), 3.83 (d, J=11.2 Hz, 3/2H ), 3.80 (d, J=11.2 Hz, 3/2H), 3.81 (m, 1H), 3.54 (ddd, J=1.0, 6.1, 6.1 Hz, 2/2H), 3.54 (ddd, J=1.0, 6.1, 6.1 Hz, 2/2H), 2.04 (m, 2H), 1.77 (m,2H), 1.44 (s, 9H), 1.35–1.28 (m, 12H); $^{13}$C NMR (CDCl$_3$, 100 MHz) δ: 160.2, 155.6, 134.8, 128.5, 128.0, 122.2 (q, J$_{C-F}$=274.6 Hz), 120.6, 114.8, 79.7, 72.4, 68.1, 66.9 (m, 2C), 54.7 (m, 2C), 32.2, 29.4, 29.3, 29.2, 29.0, 29.0, 28.3, 25.9.

EXAMPLE 5

Synthesis of N-acylphosphate (22)

To N-Boc-phosphate (21) (489 mg, 0.657 mmol) in dichloromethane (3.28 mL) was added at 0° C. trifluoroacetic acid (1.31 mL) and the mixture was stirred at the same temperature for 5 hours. The reaction mixture was concentrated under reduced pressure and the residue was dissolved in THF (3.28 mL). To the solution were added triethylamine and 4-nitrophenyl hexadecanoate (372 mg, 0.985 mmol) at 0° C. The mixture was stirred at room temperature for 1 day and then concentrated under reduced pressure. The residue was purified with silica gel column chromatography (from 0 to 2% methanol in chloroform) to give N-acylphosphate (22) (355 mg, 61.2%).

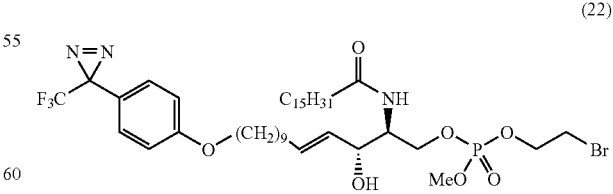

$[\alpha]_D^{22.0}$ −1.86 (c=0.892, CHCl$_3$) IR (KBr disk): 3302.43, 1649.29, 1520.04, 1261.56, 1184.40, 1045.51 cm$^{-1}$ $^1$H NMR (CDCl$_3$, 400 MHz) δ: 7.13 (md, J=9 Hz, 2H), 6.88 (md, J=9 Hz, 2H), 6.17 (d, J=7.6 Hz, 1H), 5.75 (td, J=6.8, 15.4 Hz, 1H), 5.49 (dd, J=6.6, 15.4 Hz, 1H), 4.33 (m, 3H), 4.17 (m, 3H), 3.94 (t, J=6.6 Hz, 2H), 3.81 (d, J=11.2 Hz, 3/2H ), 3.81 (d, J=11.2 Hz, 3/2H), 3.54 (ddd, J=0.7, 6.1, 6.1 Hz, 2/2H), 2.20 (dt, J=2.2, 8.1, Hz. 2H), 2.03 (td, J=6.8, 6.8 Hz, 2H), 1.77 (m,2H), 1.44–1.28 (m, 36H), 0.88 (t, J=6.8 Hz, 3H); $^{13}$C NMR (CDCl$_3$, 100 MHz) δ: 173.6, 160.2, 134.9, 128.5, 128.1, 122.2 (q, $J_{C-F}$=274.6 Hz), 120.6, 114.8, 72.5, 68.1, 67.1 (m), 66.8 ($J_{C-P}$=5.8 Hz), 54.8 ($J_{C-P}$=5.8 Hz), 53.8 ($J_{C-P}$=5.0 Hz), 36.8, 32.3, 31.9, 29.7, 29.6, 29.5, 29.5, 29.4, 29.3, 29.3, 29.2, 29.1, 26.0, 25.7, 22.7, 14.1.

EXAMPLE 6

Synthesis of TFDP-sphingomyelin (23)

To N-Acylphosphate (22) (200 mg, 0.227 mmol) in methanol (2.3 mL) was added a 30% aqueous trimethylamine solution (2.3 mL) at room temperature and the mixture was stirred for 1 day. The reaction mixture was concentrated under reduced pressure. The residue was dissolved in chloroform and methanol, and washed with water. The organic layer was concentrated under reduced pressure, and the residue was purified with silica gel column chromatography (25% methanol in chloroform, chloroform:methanol:H$_2$O=65:25:4) to give TFDP-sphingomyelin (23) (136 mg, 70.8%).

(23)

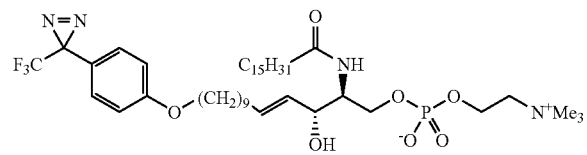

$[α]_D^{23.0}$ 0.741 (c=0.594, CHCl$_3$) IR (KBr disk): 3364.16, 1639.64, 1520.04, 1234.55, 1153.54, 1087.95 cm$^{-1}$ $^1$H NMR (CD$_3$OD, 400 MHz) δ: 7.16 (md, J=9 Hz, 2H), 6.96 (md, J=9 Hz, 2H), 5.71 (td, J=6.8, 15.4 Hz, 1H), 5.46 (dd, J=7.6, 15.4 Hz, 1H), 4.27 (m, 2H), 4.13–4.03 (m, 4H), 4.05 (t, J=6.3 Hz, 2H), 3.64 (m, 2H), 3.23 (s, 9H), 2.18 (m, 2H), 2.03 (td, J=6.8, 6.8 Hz, 2H), 1.76 (m,2H), 1.59–1.26 (m, 34H), 0.88 (t, J=6.6 Hz, 3H); $^{13}$C NMR (CD$_3$OD, 100 MHz) δ: 175.8, 161.9, 135.0, 131.3, 129.2, 123.7 (q, $J_{C-F}$=273.8 Hz), 121.4, 116.2, 72.5, 69.2, 67.4 (m), 65.9 ($J_{C-P}$=5.8 Hz), 60.4 ($J_{C-P}$=5.0 Hz), 55.3 ($J_{C-P}$=6.6 Hz), 54.73, 54.70, 54.67, 33.5, 33.3, 33.0, 30.8, 30.8, 30.7, 30.7, 30.6, 30.6, 30.5, 30.5, 30.4, 30.3, 30.2, 28.9, 27.2, 27.1, 23.7, 14.5. FAB HRMS m/z calcd for C$_{43}$H$_{74}$F$_3$N$_4$NaO$_7$P (M+Na$^+$) 869.5145, found 869.5147.

EXAMPLE 7

Synthesis of Alcohol (24)

Methyl 10-undecenoate (1.50 g, 7.56 mmol) in dichloromethane and methanol (45.4 mL, 1:1) was stirred at −78° C. for 1 hour while introducing ozone thereto. Nitrogen gas was introduced thereto for 5 minutes to remove ozone and then thereto was added sodium borohydride (429 mg, 11.4 mmol). The mixture was stirred for 8 hours while gradually rising to room temperature. To the reaction mixture was added an aqueous saturated ammonium chloride solution and after neutralizing, the mixture was concentrated under reduced pressure. The residue was extracted with ethyl acetate and the organic layer was washed with an aqueous saturated sodium chloride solution. The organic layer was dried over anhydrous magnesium sulfate, concentrated under reduced pressure and the residue was purified with silica gel column chromatography (from 25% to 33% ethyl acetate in hexane) to give Alcohol (24) (1.40g, 91.3%).

(24)

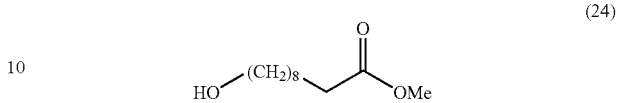

IR (NaCl neat): 3385.38, 1739.95, 1437.10, 1172.83, 1057.09 cm$^{-1}$ $^1$H NMR (CDCl$_3$, 400 MHz) δ: 3.67 (s, 3H), 3.63 (t, J=6.8 Hz, 2H), 2.30 (t, J=7.6 Hz, 2H), 1.93 (brs, 1H), 1.64 (m, 2H), 1.55 (m, 2H), 1.30 (m, 10H); $^{13}$C NMR (CDCl$_3$, 100 MHz) δ: 174.3, 62.8, 51.4, 34.0, 32.7, 29.3, 29.3, 29.1, 29.0, 25.6, 24.8.

EXAMPLE 8

Synthesis of TFDP-ester (25)

To Alcohol (24) (150 mg, 0.742 mmol) in THF (2.2 mL) were added at 0° C. triphenylphosphine (233 mg, 0.890 mmol) and diisopropyl azodicarboxylate (0.19 mL, 0.96 mmol), followed by adding Phenol (19) (240 mg, 1.19 mmol) in THF (1.48 mL), and the mixture was stirred at room temperature for 1.5 hours. Then, the solvent of the reaction mixture was removed under reduced pressure and the residue was purified with silica gel column chromatography (5% ethyl acetate in hexane) to give TFDP-ester (25) (278 mg, 96.9%).

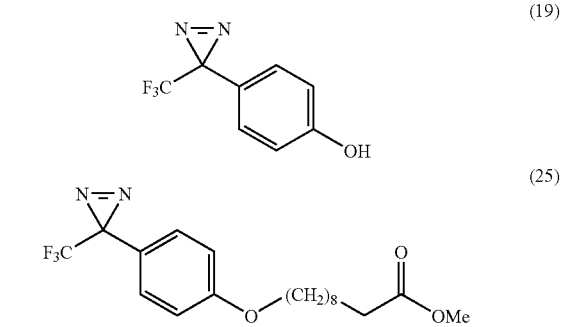

IR (NaCl neat): 1739.95, 1614.56, 1520.04, 1234.55, 1180.54 cm$^{-1}$ $^1$H NMR (CDCl$_3$, 400 MHz) δ: 7.13 (md, J=9 Hz, 2H), 6.88 (md, J=9 Hz, 2H), 3.94 (t, J=6.6 Hz, 2H), 3.66 (s, 3H), 2.30 (t, J=7.6 Hz, 2H), 1.76 (m, 2H), 1.61 (m, 2H), 1.45–1.31 (m, 10H); $^{13}$C NMR (CDCl$_3$, 100 MHz) δ: 174.3, 160.2, 128.1, 122.2 (q, $J_{C-F}$=274.6 Hz), 120.6, 114.8, 68.1, 51.4, 34.1, 29.3, 29.2, 29.1, 29.1, 25.9, 24.9.

EXAMPLE 9

Synthesis of TFDP-acid anhydride (26)

To TFDP-ester (25) (10.35 g, 26.8 mmol) in methanol (134 mL) was added 2N-aqueous potassium hydroxide solution (53.5 mL) and the mixture was stirred for 24 hours. The reaction mixture was acidified with 2N-hydrochloric acid, and the mixture was extracted with ethyl acetate. The organic layer was washed with an aqueous saturated sodium chloride solution, dried over anhydrous magnesium sulfate and concentrated under reduced pressure to give TFDP-carboxylic acid. To thus obtained TFDP-carboxylic acid (476 mg, 1.23 mmol) in THF (4.91 mL) were added triethylamine (0.22 mL, 1.47 mmol) and pivaloylchloride (0.14 mL, 1.18 mmol) successively and the mixture was stirred for 15 minutes. To the reaction mixture was added an aqueous saturated ammonium chloride solution and the mixture was extracted with ethyl acetate. The organic layer was washed with an aqueous saturated sodium chloride solution, dried over anhydrous magnesium sulfate and concentrated under reduced pressure to give TFDP-carboxylic acid anhydride (26). Thus obtained TFDP-carboxylic acid anhydride (26) was subjected to the following reaction without purification.

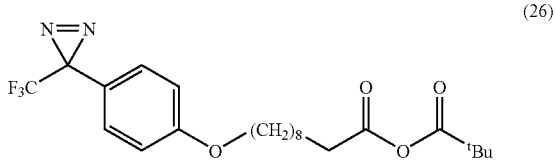

(26)

EXAMPLE 10

Synthesis of N-Boc-phosphate (28)

To carbon tetrabromide (0.375 mmol, 124 mg) in pyridine (1.3 mL) was added at 0° C. 2-bromoethyl dimethyl phosphite (0.056 mL, 0.375 mmol), followed by adding N-Boc-sphingosine (27) (100 mg, 0.250 mmol). The mixture was stirred for 3.5 hours while gradually rising to room temperature. The reaction mixture was filtered. The filtrate was acidified with 2N-hydrochloric acid and extracted with ethyl acetate. The organic layer was washed with 2N-hydrochloric acid, an aqueous saturated sodium hydrogencarbonate solution and an aqueous saturated sodium chloride solution, successively. The organic layer was dried over anhydrous magnesium sulfate, and concentrated under reduced pressure. The residue was purified with silica gel column chromatography (from 33% to 50% ethyl acetate in hexane) to give N-Boc-phosphate (28) (133 mg, 88.7%).

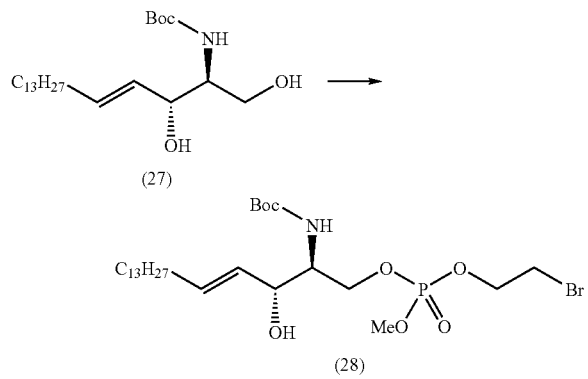

$[\alpha]_D^{22.0}$ 2.58 (c=1.021, CHCl$_3$) IR (NaCl neat): 3387.31, 1712.94, 1521.97, 1460.25, 1259.63, 1174.75, 1024.29 cm$^{-1}$ 1H NMR (CDCl$_3$, 400 MHz) δ: 5.76 (td, J=6.8, 15.4 Hz, 1H), 5.50 (dd, J=7.1, 15.4 Hz, 1H), 5.05 (brs, 1H), 4.36–4.31 (m, 3H), 4.16 (m, 2H), 3.82 (d, J=11.2 Hz, 3/2H), 3.82 (d, J=11.2 Hz, 3/2H), 3.79 (m, 1H), 3.55 (dd, J=6.1, 6.1 Hz, 2H), 2.04 (m, 2H), 1.44 (s, 9H), 1.26 (m, 22H), 0.88 (t, 6.8 Hz, 3H); $^{13}$C NMR (CDCl$_3$, 100 MHz) δ: 155.6, 134.9, 128.5, 79.7, 72.4, 66.9 (m, 2C), 54.7 (m, 2C), 32.3, 31.9, 29.6, 29.6, 29.5, 29.3, 29.2, 29.1, 28.3, 22.6, 14.1.

EXAMPLE 11

Synthesis of N-Acylphosphate (29)

To N-Boc-phosphate (28) (590 mg, 0.982 mmol) in dichloromethane (4.9 mL) was added trifluoroacetic acid (1.96 mL) at 0° C. and the mixture was stirred for 1.5 hours at the same temperature. The reaction mixture was concentrated under reduced pressure. To the residue in THF and H$_2$O (9.82 mL, 1:1) were added potassium carbonate (679 mg, 4.91 mmol) and the above TFDP-carboxylic acid anhydride (26) (1.18 mmol) at 0° C. successively, and the mixture was stirred for 45 minutes. To the reaction mixture was added an aqueous saturated aqueous ammonium chloride solution and the mixture was extracted with ethyl acetate. The organic layer was washed with an aqueous saturated sodium hydrogencarbonate solution, dried over anhydrous magnesium sulfate, and concentrated under reduced pressure. The residue was purified with silica gel column chromatography (from 0 to 2% methanol in chloroform) to give N-Acylphosphate (29) (678 mg, 80.7%).

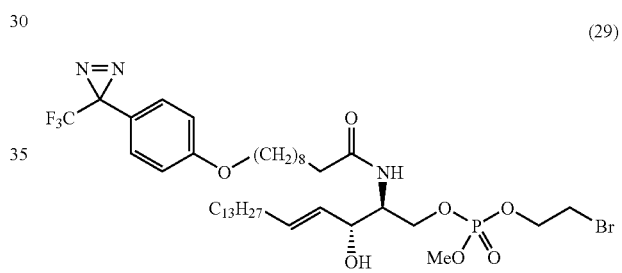

(29)

$[\alpha]_D^{21.5}$ −2.53 (c=1.065, CHCl$_3$) IR (KBr disk): 3294.71, 1643.50, 1520.04, 1259.63, 1184.40, 1151.61, 1055.16 cm$^{-1}$ 1H NMR (CDCl$_3$, 400 MHz) δ: 7.13 (md, J=9 Hz 2H), 6.88 (md, J=9 Hz, 2H), 6.27 (d, J=7.6 Hz, 1H), 5.75 (td, J=6.8, 15.4 Hz, 1H), 5.48 (dd, J=6.6, 15.4 Hz, 1H), 4.36–4.30 (m, 3H), 4.18 (m, 3H), 3.94 (t, J=6.6 Hz, 2H), 3.81 (d, J=11.2 Hz, 3/2H), 3.80 (d, J=11.2 Hz, 3/2H), 3.54 (ddd, J=0.7, 6.1, 6.1 Hz, 2H), 2.20 (dt, J=2.2, 8.1, Hz. 2H), 2.03 (m, 2H), 1.76 (m, 2H), 1.62 (m, 2H), 1.45–1.20 (m, 32H), 0.88 (t, J=6.6 Hz, 3H); $^{13}$C NMR (CDCl$_3$, 100 MHz) δ: 173.7, 160.2, 135.0, 128.4, 128.0, 122.2 (q, J$_{C-F}$=274.6 Hz), 120.6, 114.8, 72.5, 68.1, 67.1 (m), 66.8 (J$_{C-P}$=5.79 Hz), 54.8 (m), 53.7, 36.7, 32.3, 31.9, 29.7, 29.6, 29.6, 29.5, 29.5, 29.3, 29.2, 29.1, 29.1, 27.4, 25.9, 25.6, 22.7, 14.1.

EXAMPLE 12

Synthesis of TFDP-sphingomyelin (30)

To N-Acylphosphate (29) (200 mg, 0.234 mmol) in methanol (2.3 mL) was added a 30% aqueous trimethylamine solution (2.3 mL) at room temperature and the mixture was stirred for 1 day. The reaction mixture was concentrated under reduced pressure. The residue was dissolved in chloroform and methanol, and washed with water.

The organic layer was concentrated under reduced pressure and purified with silica gel column chromatography (25% methanol in chloroform, chloroform:methanol: H$_2$O=65:25: 4) to give TFDP-sphingomyelin (30) (112 mg, 58.3%).

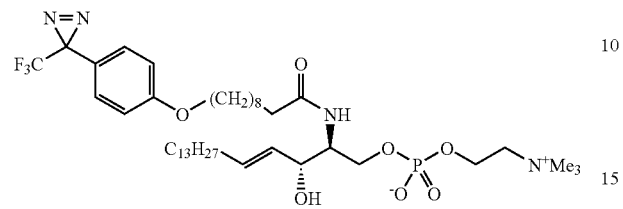

(30)

$[\alpha]_D^{23.0}$ −1.59 (c=0.724, CHCl$_3$) IR (KBr disk): 3423.96, 1639.64, 1520.04, 1234.55, 1087.95 cm$^{-1}$ $^1$H NMR (CD$_3$OD, 400 MHz) δ: 7.16 (md, J=9 Hz, 2H), 6.97 (md, J=9 Hz, 2H), 5.71 (td, J=6.8, 15.4 Hz, 1H), 5.45 (dd, J=7.6, 15.4 Hz, 1H), 4.27 (m, 2H), 4.12–3.95 (m, 4H), 3.98 (t, J=6.3 Hz, 2H), 3.63 (m, 2H), 3.22 (s, 9H), 2.18 (m, 2H), 2.02 (td, J=6.8, 6.8 Hz, 2H), 1.77 (m, 2H), 1.58 (m, 2H), 1.47–1.26 (m, 32H), 0.88 (t, J=6.8 Hz, 3H); $^{13}$C NMR (CD$_3$OD, 100 MHz) δ: 1775.9, 162.0, 135.1, 131.2, 129.2, 123.8 (q, J$_{C-F}$=273.8 Hz), 121.4, 116.2, 72.6, 69.2, 67.5 (m), 65.8 (J$_{C-P}$=5.0 Hz), 60.4 (J$_{C-P}$=5.0 Hz), 55.3 (J$_{C-P}$=6.6 Hz), 54.73, 54.69, 54.66, 37.3, 33.5, 33.1, 30.8, 30.8, 30.8, 30.7, 30.6, 30.5, 30.5, 30.4, 30.3, 27.1, 23.7, 14.4. FAB HRMS m/z calcd for C$_{41}$H$_{70}$F$_3$N$_4$NaO$_7$P (M+Na$^+$) 841.4832, found 841.4866.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A photoaffinity-labeled sphingomyelin analog of the following formula,

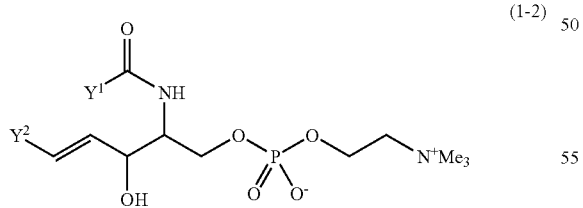

(1-2)

wherein Y$^1$ and Y$^2$ are different from each other and are R$^5$ or Z—O—R$^1$, and said R$^5$ is C$_{1-20}$ alkyl group, aryl group or C$_{1-6}$ alkyl group substituted by aryl group, said Z is 4-(3-trifluoromethyl-3H-diazirin-3-yl)-phenyl group, said R$^1$ is C$_{1-20}$ alkylene group and Me is methyl group, or an optically active compound thereof.

2. A photoaffinity-labeled sphingomyelin analog of the following formula,

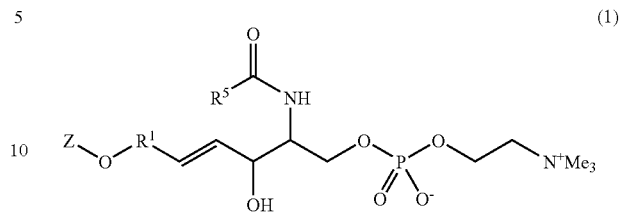

(1)

wherein R$^1$ is C$_{1-20}$ alkylene group, R$^5$ is C$_{1-20}$ alkyl group, aryl group or C$_{1-6}$ alkyl group substituted by aryl group, Z is 4-(3-trifluoromethyl-3H-diazirin-3-yl)-phenyl group and Me is methyl group, or an optically active compound thereof.

3. The analog or optically active compound thereof according to claim 2, wherein R$^1$ is C$_{7-16}$ alkylene group, and R$^5$ is C$_{7-16}$ alkyl group.

4. A photoaffinity-labeled sphingomyelin analog of the following formula,

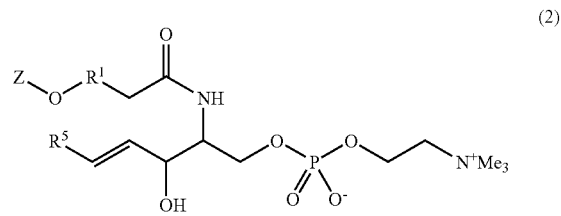

(2)

wherein R$^1$ is C$_{1-20}$ alkylene group, R$^5$ is C$_{1-20}$ alkyl group, aryl group or C$_{1-6}$ alkyl group substituted by aryl group, Z is 4-(3-trifluoromethyl-3H-diazirin-3-yl)-phenyl group and Me is methyl group, or an optically active compound thereof.

5. The analog or optically active compound thereof according to claim 4, wherein R$^1$ is C$_{7-16}$ alkylene group, and R$^5$ is C$_{7-16}$ alkyl group.

6. A process for preparing a photoaffinity-labeled sphingomyelin analog of the following formula,

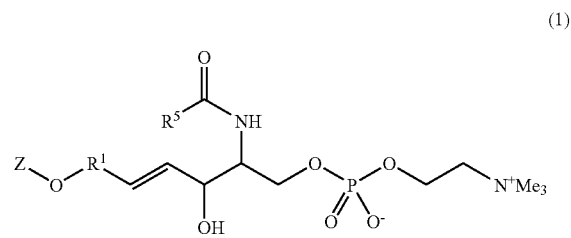

(1)

wherein R$^1$ is C$_{1-20}$ alkylene group, R$^5$ is C$_{1-20}$ alkyl group, aryl group or C$_{1-6}$ alkyl group substituted by aryl group, Z is 4-(3-trifluoromethyl-3H-diazirin-3-yl)-phenyl group and Me is methyl group, or an optically active compound thereof, which comprises deprotecting hydroxy protecting group (P$^1$) of a compound of the following formula (3),

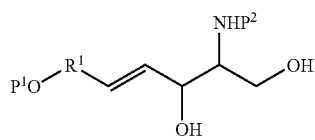

wherein P¹ is hydroxy protecting group, P² is amino protecting group and R¹ is the same as defined above, to prepare a triol compound represented by the following formula (4),

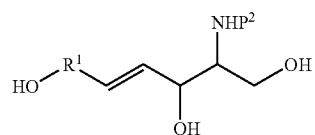

wherein R¹ and P² are the same as defined above, acetalizing the compound (4) to prepare a compound of the following formula (5),

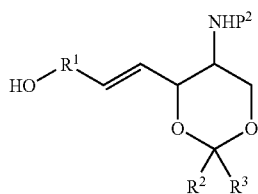

wherein $R^2$ and $R^3$ are the same or different and are hydrogen atom, $C_{1-4}$ alkyl group or phenyl group, or $R^2$ and $R^3$ may be taken together to form $C_{3-6}$ cycloalkyl group, and $R^1$ and $P^2$ are the same as defined above, reacting the compound (5) with a compound having 4-(3-trifluoromethyl-3H-diazirin-3-yl)-phenyl group, subjecting the compound to deacetonide reaction to prepare a compound of the following formula (6),

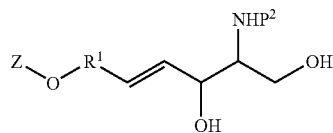

wherein R¹, P² and Z are the same as defined above, and then reacting the compound (6) with 2-halogenoethyl dialkyl phosphite to prepare a compound of the following formula (7),

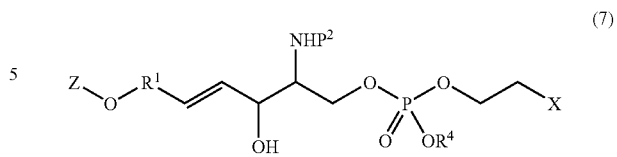

wherein $R^4$ is $C_{1-6}$ alkyl group, X is a halogen atom and $R^1$, $P^2$ and Z are the same as defined above, deprotecting amino group (P²) of the compound (7) and then subjecting the compound to amidation reaction to prepare a compound of the following formula (8),

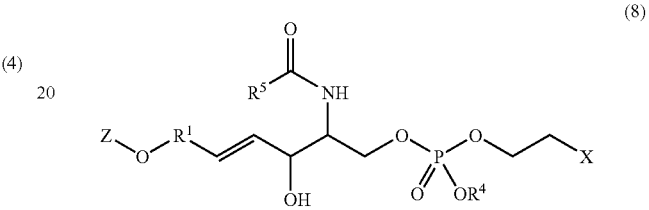

wherein $R^5$, X, Z, $R^1$ and $R^4$ are the same as defined above, substituting X of the compound (8) with trimethylamine, and hydrolyzing the phosphate to prepare the compound (1).

7. A process for preparing a photoaffinity-labeled sphingomyelin analog of the following formula (2),

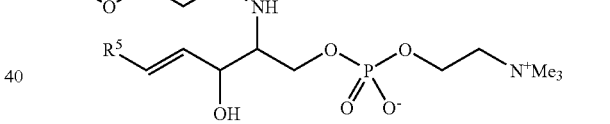

wherein $R^1$ is $C_{1-20}$ alkylene group, $R^5$ is $C_{1-20}$ alkyl group, aryl group or $C_{1-6}$ alkyl group substituted by aryl group, Z is 4-(3-trifluoromethyl-3H-diazirin-3-yl)-phenyl group and Me is methyl group, or an optically active compound thereof, which comprises reacting a compound of the formula (9),

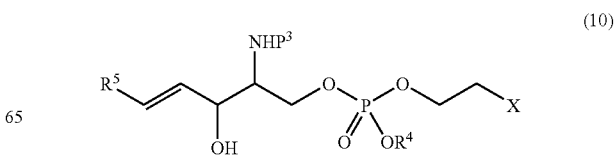

wherein P³ amino protecting group and R⁵ is the same as defined above, with 2-halogenoethyl dialkyl phosphite to prepare a compound of the following formula (10),

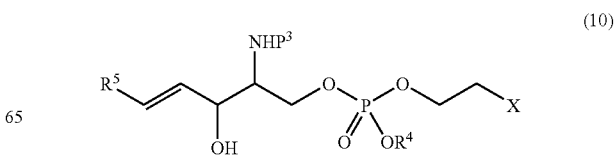

wherein $R^4$ is $C_{1-6}$ alkyl group, X is a halogen atom, and $R^5$ and $P^3$ are the same as defined above, deprotecting amino group ($P^3$) of the compound (10), reacting the compound with a compound of the following formula (11),

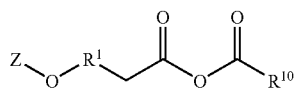

(11)

wherein and $R^{10}$ is $C_{1-6}$ alkyl group and $R^1$ and Z are the same as defined above, to prepare a compound of the formula (12),

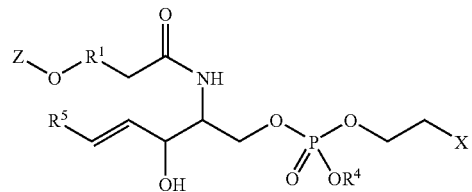

(12)

wherein X, Z, $R^4$, $R^5$ and $R^1$ are the same as defined above, substituting X of the compound (12) with trimethylamine and then hydrolyzing the phosphate to prepare the compound (2).

* * * * *